United States Patent [19]

Lieberman

[11] 4,423,728
[45] Jan. 3, 1984

[54] CAM-GUIDED TREPHINE

[76] Inventor: David M. Lieberman, 174 8th Ave., Brooklyn, N.Y. 11215

[21] Appl. No.: 352,523

[22] Filed: Feb. 26, 1982

[51] Int. Cl.³ .............................................. A61B 17/16
[52] U.S. Cl. ................................... 128/310; 33/27 K; 33/27 R
[58] Field of Search ...................... 128/305, 305.1, 310; 33/27 H, 27 K, 30 D, 21 B; 30/300, 321; 83/565

[56] References Cited

U.S. PATENT DOCUMENTS

| | | | |
|---|---|---|---|
| 2,249,906 | 7/1941 | Longovia | 128/305 |
| 3,537,345 | 11/1970 | Luppino | 33/27 K |
| 3,628,522 | 12/1971 | Kato | 30/300 |
| 4,085,508 | 4/1978 | Gyongyosi | 33/27 K |
| 4,205,682 | 6/1980 | Crock | 128/305 |
| 4,342,951 | 8/1982 | Muller | 128/305 |

OTHER PUBLICATIONS

"A New Corneal Trephine" Liberman, M.D., American Journal of Opthamology, May, 1976, pp. 684–685.

Primary Examiner—C. Fred Rosenbaum
Assistant Examiner—J. L. Kruter
Attorney, Agent, or Firm—Hedman, Casella, Gibson, Costigan and Hoare

[57] ABSTRACT

A cam-guided trephine for selectively cutting a portion of an eye provides a first, vertically disposed blade to provide an annular cut of essentially any practical shape, diameter and depth, while concurrently allowing a second, angled blade, to simultaneously provide a circular cut of substantially any practical angle, diameter, and depth. Each of the blades may be individually controlled by the surgeon, alternately and progressively lowered onto the eye during series of rotations.

17 Claims, 11 Drawing Figures

CAM-GUIDED TREPHINE

BACKGROUND OF THE INVENTION

The present invention is directed to a corneal trephine, or a surgical instrument used to cut a circular portion of the cornea.

Corneal trephines have been used in lamellar and penetrating keratoplasty. Originally, such trephines have been in the form of a honed cylinder as developed by Castroviejo. Many surgeons have attempted to improve the techniques as developed by Castroviejo. See Kadesdy DR: An electric automatic trephine, Am J Ophthalmol 34:1038, 1951; Draeger J: Ein neuer Motortrepan fuer die Kertoplastik, Berl Dtsch Ophthalmol Ges 71:318, 1972; Drews RC: Corneal trephine, Trans Am Acad Ophthalmol Otolaryngol 78:223, 1974; Draeger J: Ein Halbautomatisches electrisches Keratom fuer die Lamellaere Keratoplastik, Klin Monatsbl Augenheilkd 167:353, 1975; Crock GW, Pericic L, Rajendrana B, et al: A new system of microsurgery for human and experimental grafting, Br J Ophthalmol 62:74, 1978; Donaldson: A new corneal trephine, Presented at the July 1978 Meeting of the Ophthalmological Society of the United Kingdom, July 1978; Smirmaul H, Casey TA: A clear view trephine and lamellar dissector for corneal grafting, Am J Ophthalmol 90:92, 1980; Hessburg PC, Barron M: A disposable corneal trephine, Ophthalmic Surg 11:10, 1980.

Further, major surgical companies have attempted to make holders for such cylinders in order to improve the visualization of the cutting edge but such attempts have generally been insufficient due to lack of proper centering, obscuration of the cutting edge at sometime during the procedure, independent eye and trephine movements, and lack of ability to cut other than round windows.

An improved corneal trephine was developed by David M. Lieberman, M.D., as described in the American Journal of Opthalmology, May 1976, pages 684-685. As described therein, the surgical instrument was comprised of inner and outer cones, the inner revolving within the outer cone. The outer cone included an upper ridge held by the non-dominant hand of the surgeon, stabilizing the instrument on the eye, and a lower ridge containing an annular suction device which firmly held the eye with a pressure of from 10-15 mm Hg to assure centration. The inner cone revolved within the outer cone and carried a slide mechanism with an attached disposable razor blade. To perform the incision, the inner cone which carried the blade was rotated about the cornea. After each rotation, the blade was lowered a few thousands of an inch by turning a screw and the inner cone was rotated again. Both sides of the incision could be viewed through an operating microscope. The slide mechanism upon which the blade was mounted was controlled by an adjustment screw for precisely varying the lateral position of the blade. Two interchangeable cutters could be used, one at a time. The first provided the razor blade at a 20° angle. The second cutter held the blade vertically and was suitable for keratoplasty in which a donor cornea had been "punched." Either cutter can be used for lamellar grafts.

Although the single point trephine described in the above article by David M. Lieberman represented a significant advance in the art, only a single one of the cutters could be used at any given time. Therefore, two varied incisions could not be achieved simultaneously. Additionally, the prior art trephines could only provide a round cut and consequently could not be employed whenever an other than round incision was required.

OBJECTS AND SUMMARY OF THE INVENTION

It is therefore an object of the invention to provide a corneal trephine which overcomes the disadvantages of the prior art trephines.

It is a further object to provide a corneal trephine having a pair of blades rotatably mounted within a support structure for providing a pair of cuts to make a 360° wedge resection of the cornea.

It is a further object of the invention to provide a corneal trephine which includes a blade which can provide an "other than round" cut of the cornea, if so desired.

It is a further object of the invention to provide a corneal trephine having a first vertically disposed blade which may be adapted to provide an other than round cut, and a second blade selectively disposed at a variable angle for providing a round cut.

In accordance with the most basic aspect of the invention, the corneal trephine comprises a base, a non-circular pattern device operatively connected to the base, and a rotation device adapted to be disposed and rotated on the base, the rotation device having first and second blade mounts at portions thereof for securing respective first and second cutting blades thereto. The rotation device is further adapted to operatively engage the pattern device, whereby when the rotation device is rotated on the base, the first blade mount follows a path related to the non-circular shape of the pattern device.

Ideally, the pattern device is removable from and replaceable on the base, whereby the path of the first blade mount can be varied by removing and replacing the pattern device with a different pattern device. The pattern device may be a generally annular cam.

According to a more specific aspect of the invention, the rotation device comprises a platter adapted to bear upon and rotate on the base, and a first carriage slidably mounted on the platter so as to allow the radial movement of the first carriage relative to the platter, the first blade mount being operatively connected to the first carriage. A slave device is operatively connected to the first carriage and adapted to engage the generally annular cam. A biasing device is provided for radially biasing the carriage such that the slave device comes into engagement with the annular cam, whereby the first blade mount follows a path substantially identical to the shape of the generally annular cam upon rotation of the platter on the base.

More specifically, the slave device may include a substantially round wheel which bears upon the generally annular cam and rotates as the platter is rotated. The slave device may further include a substantially vertically disposed shaft, the wheel being mounted eccentrically on the shaft, the axis of the wheel being offset from the axis of the shaft, such that the radial position of the first blade mount may be adjusted by rotating the shaft. Ideally, the generally annular cam is disposed about the outer periphery of the base, the biasing means biases the first carriage radially inward and the wheel engages the outer periphery of the generally annular cam.

The first blade mount is preferably connected to the first carriage by a generally vertically disposed screw, a portion of which is captive within the carriage, such that the vertical position of the first blade mount may be adjusted by adjusting the screw.

Still more specifically, the base may include a generally annular upper surface and the trephine may further include an outer cone-shaped structure connected at the top thereof to the base and at the bottom thereof to annular suction means adapted to be placed on the eye and substantially fixed thereto by means of suction applied thereto. The platter is preferably annular and the trephine further includes an inner cone-shaped structure disposed within the outer cone-shaped structure and connected at the top thereof to the platter, the bottom thereof being disposed adjacent to the annular suction means.

According to an additional aspect of the present invention, the rotation device referred to above may further include a second blade mount separate from the first blade mount, the second blade mount provided for securing a cutting blade thereto. The rotation device may further include apparatus for adjusting the radial, vertical and angular dispositions of the second blade mount.

More specifically, the rotation device may further include a second carriage slidably mounted on the platter so as to allow radial movement of the second carriage relative to the platter, the second blade mount being operatively connected to the second carriage, and a locking device for locking the second carriage at a selected radial position. The second blade mount may be connected to the second carriage by a variably oriented screw and a swivel mount, whereby the vertical position of the second blade mount may be adjusted by adjusting the variably oriented screw, and the angle that the second blade mount makes with respect to the vertical may be adjusted by adjusting the orientation of the swivel mount. Preferably, the swivel mount is connected to the carriage by a hinge, and a portion of the variably oriented screw is captive within the swivel mount.

BRIEF DESCRIPTION OF THE DRAWINGS

These and other objects and aspects of the invention will be described below with reference to the following drawing figures of which.

DETAILED DESCRIPTION OF THE INVENTION

Figures 1, 2:
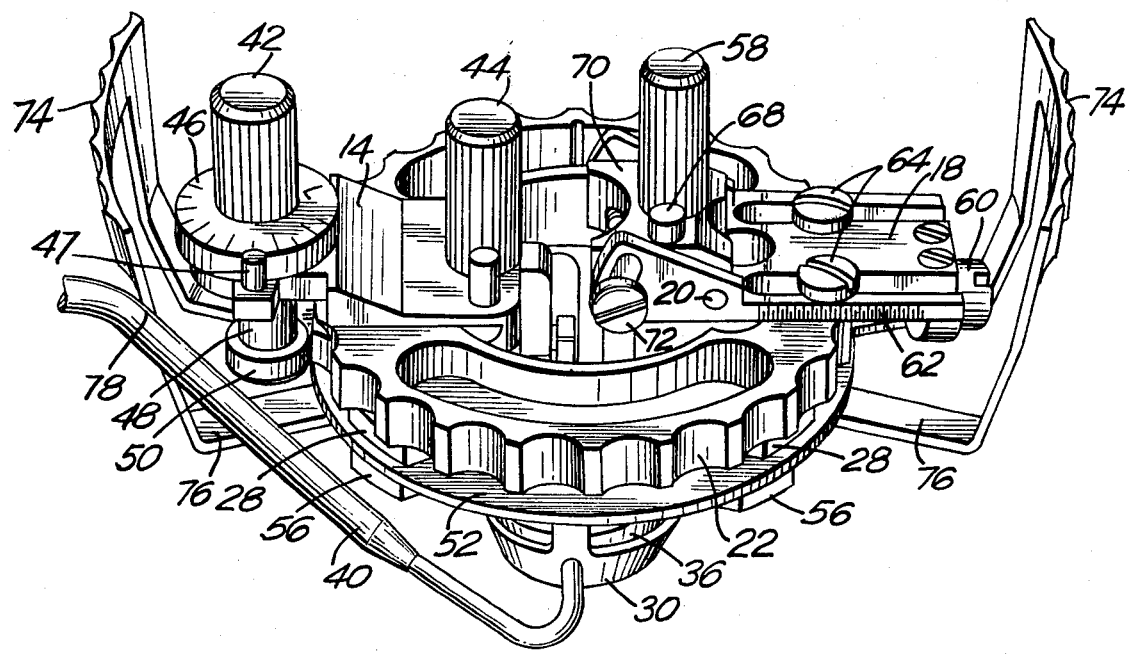
FIG. 1 is a perspective view of the cam-guided trephine in accordance with the present invention.
FIG. 2 is a bottom view of the cam-guided trephine illustrated in FIG. 1.
Figure 3:
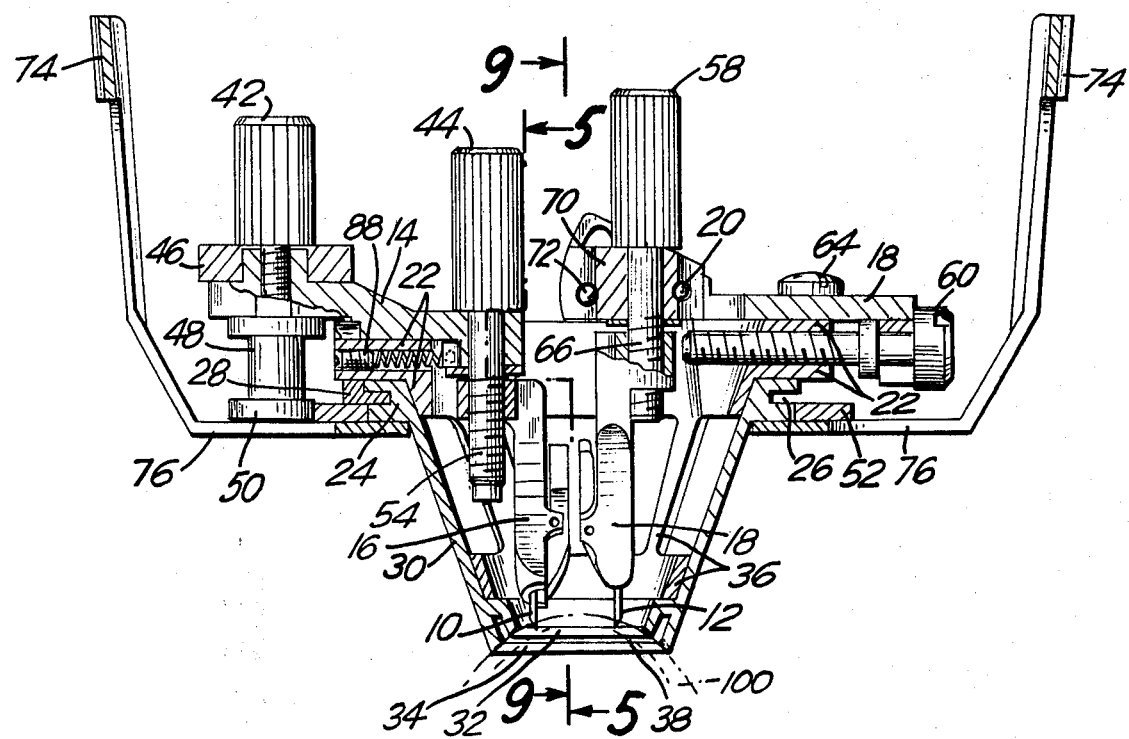
FIG. 3 is a cross-section view taken through section 3—3 of FIG. 2.

The cam-guided trephine according to the present invention will first be described with reference to FIGS. 1-3. The trephine provides a pair of surgical blades 10 and 12, blade 10 hereinafter being referred to as the "vertical" blade, blade 12 hereinafter being referred to as the "angled" blade. As best shown in FIG. 3, blade 10 is fixedly secured to vertical blade carriage 14 via vertical blade support 16. Similarly, angled blade 12 is fixedly secured to angled blade carriaged 18 via angled blade supports 19 and swivel hinge 20. Vertical blade carriage 14 and angled blade carriage 18 are slidably mounted on platter 22, best illustrated in FIG. 1. Platter 22 is, in turn, rotatably mounted on annular base 24, as best illustrated in FIGS. 2 and 3. The annular base 24 is provided with a groove 26 into which one or more stays 28 are snuggly disposed to thereby "lock" the platter 22 onto the base. By providing intermitent notches (not shown) in the top portion of the annular base 24 in substantial alignment with the plurality of stays 28, the platter and associated apparatus may be removed from the base upon proper alignment between the stays and notches.

The annular base 24 forms the upper portion of an outer cone 30 the bottom of which is formed by inner suction ring 32 and outer suction ring 34. Similarly, platter 22 forms the upper portion of inner cone 36, the bottom of which is adjacent to the suction ring assembly. The section ring assembly forms a void 38 between the inner and outer suction rings 32, 34, the void 38 being in communication with suction tube 40.

Operatively connected to the vertical blade carriage 14 is a vertical blade radial adjustment knob 42 and a vertical blade vertical adjustment knob 44. Connected to knob 42 is a graduated index plate 46, shaft 48 and slave cam 50 which eccentrically mounted on shaft 48. Slave cam 50 rests on, and is guided by an annular master cam 52 which is fixedly secured to annular base 24 by means of pins 54 provided by pin supports 56. The radial position of vertical blade 10 is thus determined by master and slave cams 52 and 50, respectively, as will be more fully explained below with reference to FIGS. 4 and 5. The vertical blade vertical adjustment knob 44 is integral with the vertical blade vertical adjustment screw 54 which is threadably secured to the vertical blade support 16 to thereby adjust the vertical position of vertical blade 10 in a manner to be more fully described with reference to FIGS. 4 and 5. A pair of sliding guide posts 55 on either side of screw 54 are provided between blade support 16 and carriage 14.

Operatively connected to the angled blade carriage 18 are an angled blade vertical adjustment knob 58 and an angled blade radial adjustment screw 60. Screw 60 is threadedly secured to platter 22 and the radial position of the angled blade 12 is determined by screw 60 in a manner to be more fully described with reference to FIGS. 6 through 9. Also provided on carriage 18 is a vernier scale 62 to indicate the radial position. Screws 64 are provided to lock the radial position of the angled blade 12 in a fixed position. Knob 58 is integral with screw 66 which in turn is threadedly secured to angled blade support 19 to provide vertical adjustment of the angled blade in a manner to be more fully described also with reference to FIGS. 6 through 9. Angled blade support 19 is operatively connected to the angled blade carriage 18 by way of screw 66, a pair of sliding guide posts 68 on either side of screw 66 and swivel mount 70 which is hingedly secured to the carriage 18 by way of hinge 20. Screw 66 is held captive within swivel mount 70 such that screw 66, guide posts 68 and angled blade support 18 may rotate about hinge 20 when lock screws 72 are loosened, in order to provide a particular angle for the angled blade in a manner to be more fully described below with reference to FIGS. 6 through 9.

Finally, a pair of radially opposed finger grips 74 are secured to the bottom of the annular base 24 by way of upwardly extending posts 76. Preferably, one of the finger grips 74 is configured so as to include a portion of, and thereby support, the suction tube 40, as illustrated at point 78 of finger grip 74. Unlike the prior art single point trephine described above, the finger grips 74 are angled upwardly away from the eye to provide more room to maneuver near the eye.

In operation, the radial or horizontal position of each of the blades is precisely adjusted by turning knob 42 and 60 while the angle formed by angled blade 12 is precisely adjusted by loosening lock screws 72 and tilting the swivel mount 70 as desired. Further, the shape of the section cut by vertical blade can be determined by providing a particularly shaped master cam 52.

After the above adjustments, the surgeon grasps the trephine by opposed finger grips 74 and places the apparatus onto the sclera of the patient's eye 100, as shown in FIG. 3. A partial vacuum is then provided via suction tube 40 to thereby adequately fix the eye to the inner and outer suction rings 32 and 34 usually using less than 10 cm $H_2O$ pressure thereby avoiding raising the intraocular pressure above physiological levels. The suction ring lies ahead of the rectii but outside the limbus. This area of the eye is anatomically constant, for if the ring is moved from this area just a small fraction of a millimeter, the ring will not fixate the eye. When so disposed, the position of the eye will be constant relative to the trephine, and any movements imparted to the trephine by the surgeon will cause the eye to move in concert therewith.

After properly fixing the trephine to the eye, the blades 10 and 12 may be lowered to the desired vertical level by adjusting knobs 44 and 58. The entire platter and associated apparatus including the carriages 14 and 18 and blade supports 16 and 18 are rotated about the base 24 thereby forming a pair of annular cuts of a desired shape, width, and depth. When so rotated, the bottom and outer surfaces of the platter 22 act as a bearing surface upon the top and inner surfaces of base 24. Similarly, the outer surfaces of inner cone 36 acts as a bearing surface upon the inner surface of the outer cone 30. Thus, close tolerances in the manufacture of the trephine are required. As will be appreciated, however, the accuracy and precision of the cuts provided by the blades is only limited to the precision available in machining the trephine.

Figure 10:
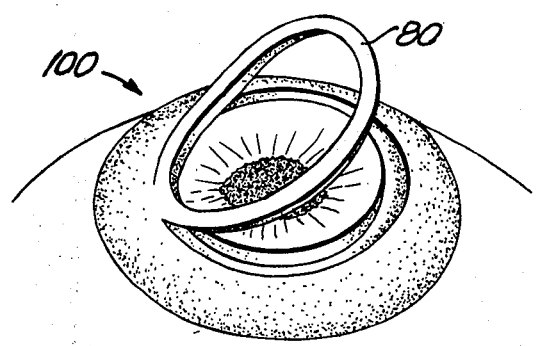
FIG. 10 is a perspective view of the section removed from the cornea by the cam-guided trephine in accordance with the present invention.
Figure 11:
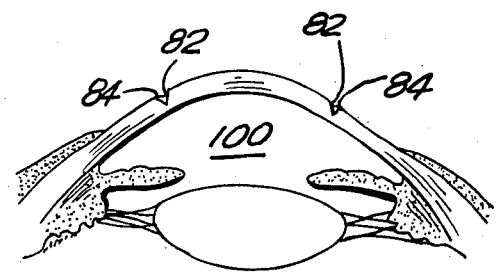
FIG. 11 is a section view of the cornea illustrating the cross-section of the wedge removed therefrom.

With brief reference to FIGS. 10 and 11, a wedge 80 may be removed from the eye utilizing the trephine in accordance with the embodiment described above. As shown in FIGS. 10 and 11 a 360° wedge resection of the cornea, whereby the vertical inner cut, 82, FIG. 11, provided by vertical blade 10 may be round, or "other than round" if "astigmatism" is present, while the outer cut 84 is appropriately angled but always round. Removal of the wedge with edge-to-edge suturing would effectively shorten the anterior chord of the cornea and thus flatten the cornea, thus providing a possible surgical treatment for high myopia. However, it should be noted that the trephine in accordance with the present invention is not in any way limited to the resectioning procedure illustrated in FIGS. 10 and 11, the trephine according to the present invention readily lending itself to other procedures as well. For example, a simple 360°0 relaxing incision that would intentionally weaken the limbal ring would be an alternative surgical treatment for low degrees of myopia.

Figures 4, 5:
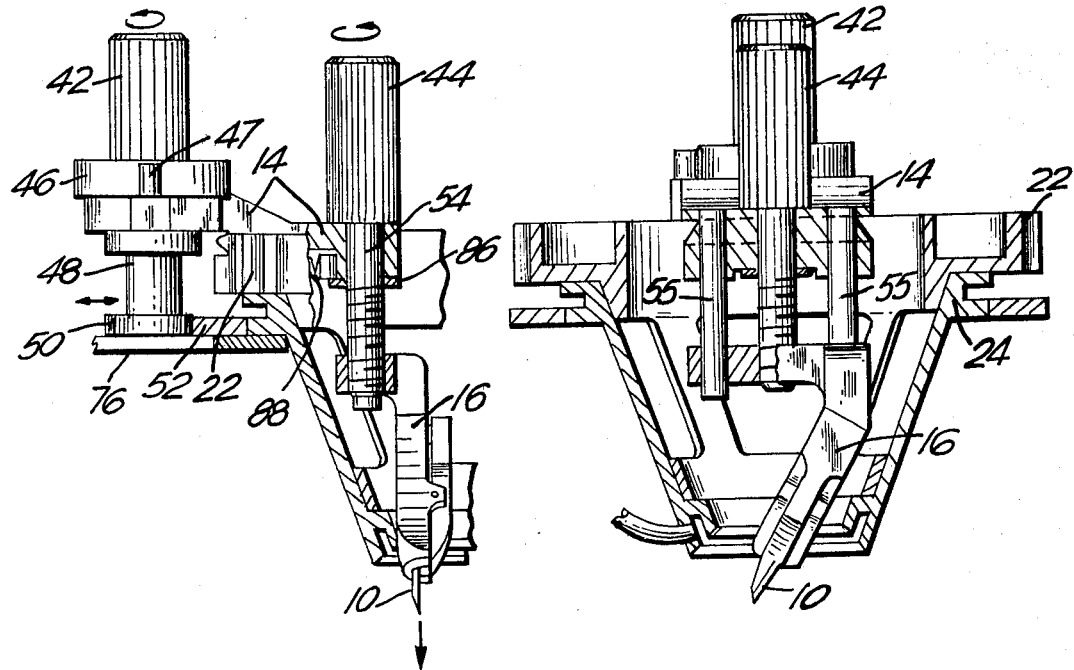
FIG. 4 is a partial cross-sectional view taken from the front of the cam guided trephine illustrating the details of the vertical blade and associated controls.
FIG. 5 is a cross-sectional view through section 5—5 of FIG. 3 illustrating the details of the vertical blade and associated controls.

Adjustment of the vertical blade 10 will now be described in more detail with reference to FIGS. 4 and 5. First with respect to the vertical adjustment of the vertical blade, knob 44 is rotated in order to rotate screw 54. Screw 54 is captive within carriage 14 by means of lock washer 86. Thus, upon turning screw 54, which threadedly engages support 16, the support is either raised or lowered relative to carriage 14. During the raising and lowering and support 16, the support is slidably guided vertically by means of sliding posts 55 which are fixedly secured to one of carriage 14 or support 16, and slidably disposed within the other, in order to assure precise vertical displacement of the vertical blade 10.

On the other hand, the radial location of the vertical blade 10 is determined by both the master cam 52 and the slave cam 50. With specific reference to FIGS. 3 and 4, it can be seen that slave cam 50 is biased radially into abuttment with master cam 52 under the force of inwardly biased spring 88 disposed within platter 22 between platter 22 and carriage 14. Thus, by removing the platter 22 and associated carriages and adjustment devices, a different master cam 52 can be disposed about the lower portion of base 24 to thereby provide upon assembly a predetermined radial position of carriage 14 and consequently vertical blade 10. In fact, it can be seen that the radial position of carriage 14 and blade 10 at any given time depends on the radial width of master cam 52 at the particular location in interest. Thus, it can now be appreciated that by providing an eliptical, or other "out of round" shape for cam 52, vertical blade 10 will cut a path having a configuration substantially identical to that provided by cam 52 upon rotation of platter 22 about base 24. Blade 10 can generate an elipse, oval or eccentric cut, or in effect, any shape window as desired. Each cut will be made as accurately and precisely as the cam 52 is machined.

The slave cam 50 is round and is mounted on shaft 48 by bearing means 90 (FIG. 2) so that upon rotation of platter 22 about base 24, cam 50 rotates smoothly about cam 52 and the entire carriage 14 smoothly follows the shape provided by cam 52. The radial location of blade 10 can further be adjusted by loosening knob 42 and rotating graduated index plate 46 to a desired position as determined relative to marker 47. Since slave cam 50 is mounted off center with respect to shaft 48 and graduated index plate 46, rotation of plate 46 and shaft 48 will effect a radial displacement of carriage 14 as slave cam 50 bears against master cam 52. In this manner, the diameter of the cut provided by blade 10 can be varied, while at the same time maintaining the shape of the cut as determined by master cam 52. The graduated index plate may provide 0.1 mm increments in ten steps thus providing a selectable diameter variation from, for example, 7.5 mm to 8.6 mm.

Figure 6:
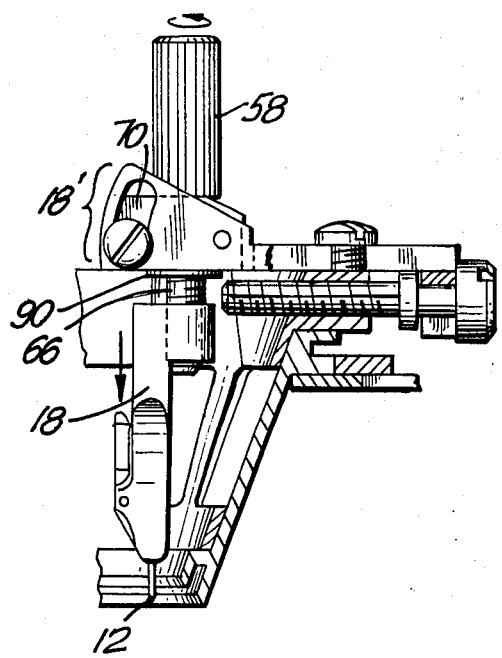
FIG. 6 is a partial cross-sectional view of the cam guided trephine taken from the front illustrating the details of the angled blade and associated controls.

The adjustment of the angled blade 12 will now be discussed with further reference to FIGS. 6-9. In a manner similar to that provided for vertical blade 10, the vertical position of angled blade 12 is provided by rotating knob 58, and consequently screw 66, which remains captive within swivel mount 70 by means of lock ring 90, such that upon rotation of screw 66 the vertical location of the angled blade support 19 may be precisely adjusted, as shown in FIG. 6.

Figure 7:
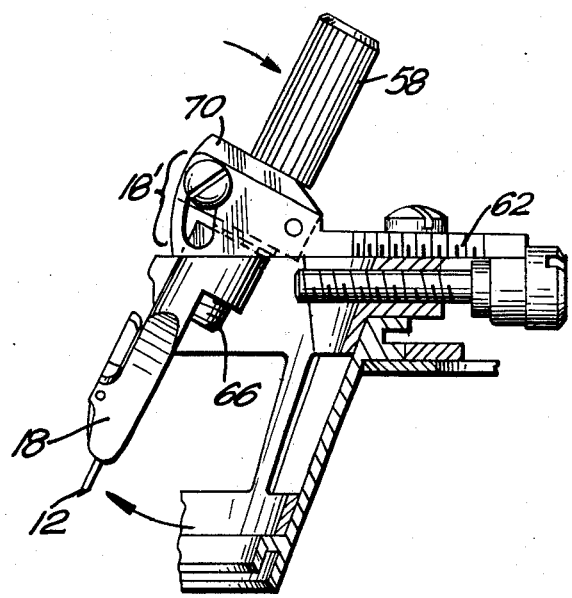
FIG. 7 is a partial cross-sectional view of the cam guided trephine illustrating the mechanism for adjusting the angle of the angled blade.

The angle with respect to the vertical that angled blade 12 can achieve is provided by the rotation of the swivel mount 70 about hinge 20. Since screw 66 is captive within swivel mount 70, the screw 66 along with blade support 19 accordingly rotates in unison with swivel mount 70. Carriage 18 is provided with a flanged portion 18' as shown in FIG. 7 (and FIG. 1). The flange 18' is provided with an arcuate hole through which lock screw 72 threadedly engages the swivel mount 70. Upon loosening the lock screw 72, the swivel mount, along with the support 18 can rotate about hinge 20 provide the appropriate angle for blade 12, at which time lock screw 72 can be tightened. Angle adjustment of from 0° to 25° is usually adequate.

Figure 8:
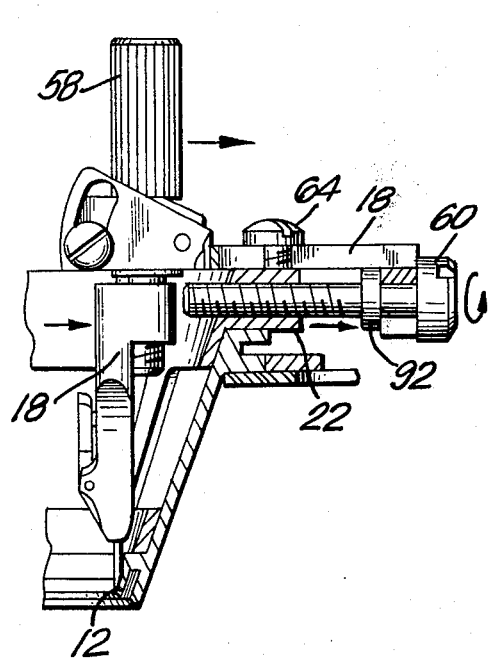
FIG. 8 is a partial cross-sectional view of the cam guided trephine illustrating the mechanism for adjusting the horozontal location of the angled blade.
Figure 9:
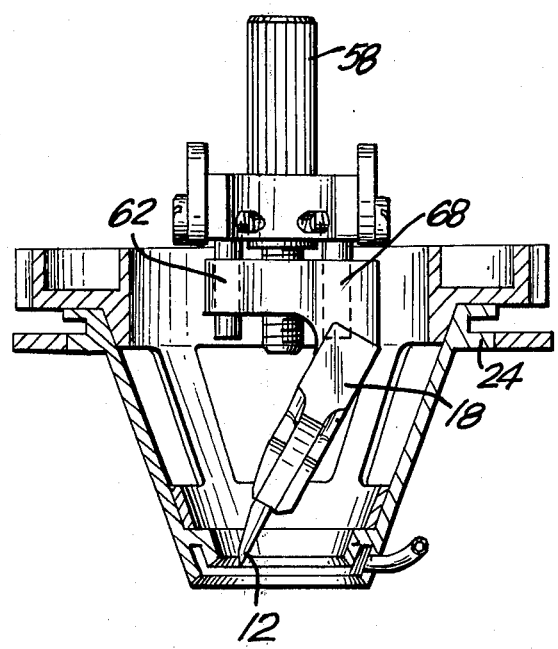
FIG. 9 is a cross-sectional view taken through section 9—9 of FIG. 3.

Finally, the radial disposition of blade 12 can be adjusted by rotating screw 60 as illustrated in FIG. 8. Screw 60 is held captive in carriage 18 by stop means 92, and thus upon loosening lock screws 64 and rotating screw 60, the carriage 18 may be moved relative to platter 22. Upon the appropriate adjustment as determined from graduated scale 62 (FIG. 1 and FIG. 7) lock screws 64 may be tightened. Finally, in FIG. 9 sliding posts 68 are illustrated and provide precise vertical movement of the blade in the same manner as that discussed with reference to the vertical blade, FIG. 5.

Thus, the cam guided trephine in accordance with the present invention provides a technique for allowing a first, vertically disposed blade to provide an annular cut of essentially any practical shape, diameter and depth, while concurrently allowing a second, angled blade, to simultaneously to provide a circular cut of substantially any practical angle, diameter, and depth. Each of the blades may be individually controlled by the surgeon, alternately and progressively lowered onto the eye during series of rotations. Although the procedures illustrated with reference to FIGS. 10 and 11 are shown as being capable with the trephine in accordance with the present invention, it will be readily apparent to those skilled in the art that other procedures may be preformed by the present invention as well, many of which require the use of only one of the two blades at a time. In such case, the blade which is not used is simply retracted vertically upward so that it does not do any cutting.

Although the invention has been described with respect to specific embodiments of the apparatus it is readily apparent than modifications, alterations, or changes may be made without departing from the spirit and scope of the invention as defined by the following claims.

What is claimed is:

1. A opthalmic device for cutting selected portions of an eye, comprising:
   base means;
   means to conform and secure the opthalmic device to the eye; first and second cutting means;
   pattern means operatively connected to said base means and having a non-circular shape; and
   rotation means adapted to be disposed and rotated on said base means, said rotation means having first and second blade mounting means at a portion thereof for securing said respective first and second cutting blades thereto, said rotation means further adapted to operatively engage said pattern means, whereby when said rotation means are rotated on said base means, said first blade mounting means follows a path related to the non-circular shape of said pattern means.

2. The device of claim 1 wherein said pattern means is removable from and replaceable on said base means, whereby said path can be varied by removing and replacing said pattern means with a different pattern means.

3. The device of claim 2 wherein said pattern means is a generally annular, non-circular cam.

4. A device of claim 3 wherein said rotation means comprises:
   a platter adapted to bear upon and rotate on said base means;
   a first carriage slidably mounted on said platter so as to allow radial movement of said first carriage relative to said platter, said first blade mounting means being operatively connected to said first carriage;
   slave means operatively connected to said first carriage and adapted to engage said generally annular cam; and
   biasing means for radially biasing said carriage such that said slave means comes into engagement with said annular cam, whereby said first blade mounting means follows a path substantially identical to the non-circular shape of said generally annular cam upon the rotation of said platter on said base means.

5. The device of claim 4 wherein said slave means includes a substantially round wheel which bears upon said generally annular cam and rotates as said platter is rotated.

6. The device of claim 5 wherein said slave means further includes a substantially vertically disposed shaft, said wheel being mounted eccentrically on said shaft, the axis of said wheel being offset from the axis of said shaft, such that the radial position of said first blade mounting means may be adjusted by rotating said shaft.

7. The device of claim 6 wherein said generally annular cam is disposed about the outer periphery of said base means, said biasing means biases said first carriage radially inward, and said wheel engages the outer periphery of said generally annular cam.

8. The device of claim 4 wherein said first blade mounting means is connected to said first carriage by a generally vertically disposed screw a portion of which is captive within said carriage, such that the vertical position of said first blade mounting means may be adjusted by adjusting said screw.

9. The device of claim 4 wherein said base means comprises a generally annular upper surface and said device further includes an outer cone-shaped structure connected at the top thereof to said base means and at the bottom thereof to annular suction means adapted to be placed on said eye and substantially fixed thereto by means of suction applied thereto.

10. The device of claim 9 wherein said platter is generally annular and said device further includes an inner cone-shaped structure disposed within the outer cone-shaped structure and connected at the top thereof to said platter, the bottom thereof being disposed adjacent said annular suction means.

11. The device of any one of claims 1-3 wherein said rotation means further includes a second blade mounting means separate from said first blade mounting means, said second blade mounting means for securing a cutting blade thereto.

12. The device of claim 11 wherein said rotation means further includes means for adjusting the radial, vertical and angular dispositions of said second blade mounting means.

13. The device of any one of claims 4-10 wherein said rotation means further comprises:
   a second carriage slidably mounted on said platter so as to allow radial movement of said second carriage relative to said platter;
   said second blade mounting means operatively connected to said second carriage; and
   means for locking said second carriage at a selected radial position.

14. The device of claim 13 wherein said second blade mounting means is connected to said second carriage by a variably oriented screw and a swivel mount whereby the vertical position of said second blade mounting means may be adjusted by adjusting said variably oriented screw, and the angle said second blade mounting means makes with respect to vertical may be adjusted by changing the orientation of said swivel mount.

15. The device of claim 14 wherein said swivel mount is connected to said carriage by a hinge, and a portion of said variably oriented screw is captive within said swivel mount.

16. The device of claims 1 or 4 further comprising a pair of finger grips connected to and disposed on opposite sides of said base, said finger grips being angled upwardly with respect to said base.

17. A opthalmic device for cutting selected portions of an eye, comprising:
   base means;
   means to conform and secure the opthalmic device to the eye, first and second cutting means;
   pattern means operatively connected to said base means and having a non-circular shape;
   a platter adapted to bear upon and rotate on said base means;
   carriage means slidably mounted on said platter so as to allow radial movement of said carriage means relative to said platter;
   blade mounting means operatively connected to said carriage means;
   slave means operatively connected to said carriage, said slave means including a substantially round, bearing-mounted wheel which bears upon, and is adpated to rotate around, said pattern means as said platter is rotated on said base means; and
   biasing means for radially biasing said carriage such that said bearing-mounted wheel engages said pattern means, whereby said blade mounting means follows a path substantially identical to the non-circular shape of said pattern means upon rotation of said platter on said base means.

* * * * *